United States Patent
Eugster et al.

(10) Patent No.: US 12,304,167 B2
(45) Date of Patent: May 20, 2025

(54) HELICAL SCREW CONVEYOR UNIT, WORM SHAFT, WORM EXTRUDER, AND METHOD FOR PROVIDING A WORM SHAFT

(71) Applicant: HITACHI ZOSEN INOVA AG, Zürich (CH)

(72) Inventors: Marc Eugster, Dällikon (CH); Adrian Schatz, Niederwangen (CH); Marc Gsponer, Schwarzenbach (CH); Patrik Gsponer, Oberuzwil (CH); Daniel Schmidt, Oberuzwil (CH)

(73) Assignee: KANADEVIA INOVA AG, Zurich (CH)

( * ) Notice: Subject to any disclaimer, the term of this patent is extended or adjusted under 35 U.S.C. 154(b) by 0 days.

(21) Appl. No.: 18/700,541

(22) PCT Filed: Oct. 12, 2022

(86) PCT No.: PCT/EP2022/078334
§ 371 (c)(1),
(2) Date: Apr. 11, 2024

(87) PCT Pub. No.: WO2023/062052
PCT Pub. Date: Apr. 20, 2023

(65) Prior Publication Data
US 2024/0416607 A1    Dec. 19, 2024

(30) Foreign Application Priority Data
Oct. 15, 2021    (EP) .................................... 21202998

(51) Int. Cl.
*B30B 9/12*    (2006.01)
*B30B 11/24*    (2006.01)
(Continued)

(52) U.S. Cl.
CPC ............ *B30B 9/121* (2013.01); *B30B 11/246* (2013.01); *B65G 33/14* (2013.01); *B65G 33/24* (2013.01); *C02F 11/121* (2013.01)

(58) Field of Classification Search
CPC ........... B30B 9/12; B30B 9/121; B30B 11/24; B30B 11/246; C02F 11/121; C02F 11/125;
(Continued)

(56) References Cited

U.S. PATENT DOCUMENTS

| 1,866,077 A | 7/1932 | Bilderback et al. |
| 3,485,341 A * | 12/1969 | Lutz ...................... B65G 33/26 198/664 |

(Continued)

FOREIGN PATENT DOCUMENTS

| CN | 201835838 U | 5/2011 |
| CN | 203112016 U | 8/2013 |

(Continued)

OTHER PUBLICATIONS

Feb. 13, 2023 Search Report issued in International Patent Application No. PCT/EP2022/078334.
(Continued)

*Primary Examiner* — Jimmy T Nguyen
(74) *Attorney, Agent, or Firm* — Oliff PLC

(57) ABSTRACT

A helical screw conveyor unit, worm shaft, worm extruder and method for providing a worm shaft, wherein the helical screw conveyor unit is an exchangeable element for a helicoidally or spirally winding helix of a worm shaft, having a main body with a helicoidally winding helix element, wherein the helical screw conveyor unit is serviced with little outlay on servicing, the top side of the lateral surface is concavely curved in shell-like form about the longitudinal axis, and the main body has a radial opening for the leadthrough of a fastening region of a worm shaft shank,
(Continued)

the helix element has at most one half of one helix turn, the the main body lateral surface has an inner surface for being seated on the fastening region, and the helical screw conveyor unit has at least one fastening element for detachably fastening the main body to the fastening region.

14 Claims, 6 Drawing Sheets

(51) Int. Cl.
  *B65G 33/14* (2006.01)
  *B65G 33/24* (2006.01)
  *C02F 11/121* (2019.01)
(58) Field of Classification Search
  CPC .......... C12M 1/00; C12M 1/26; C12M 47/10; C12M 33/16; B65G 33/14; B65G 33/24; B65G 53/08; B65G 2207/30; C02M 1/00; C02M 1/26
  See application file for complete search history.

(56) References Cited

U.S. PATENT DOCUMENTS

| | | | | |
|---|---|---|---|---|
| 3,980,013 | A * | 9/1976 | Bredeson | B30B 9/121 100/150 |
| 5,429,581 | A | 7/1995 | Michaud et al. | |
| 9,409,365 | B2 * | 8/2016 | Doppstadt | B30B 11/246 |
| 2013/0199383 | A1 * | 8/2013 | Horton | B30B 9/26 100/145 |
| 2017/0087788 | A1 | 3/2017 | Oertig et al. | |

FOREIGN PATENT DOCUMENTS

| | | |
|---|---|---|
| CN | 212831025 U | 3/2021 |
| DE | 202018103214 U1 | 6/2018 |
| EP | 0 098 340 A1 | 1/1984 |
| EP | 1 072 574 A2 | 1/2001 |
| EP | 2 792 739 A1 | 10/2014 |
| GB | 859 416 A | 1/1961 |
| JP | S58-192816 U | 12/1983 |
| JP | S62-056517 U | 4/1987 |
| JP | H10-157829 A | 6/1998 |
| KR | 10-2016-0037634 A | 4/2016 |
| WO | 2015/189271 A1 | 12/2015 |

OTHER PUBLICATIONS

Feb. 13, 2023 Written Opinion of the International Searching Authority issued in International Patent Application No. PCT/EP2022/078334.

Nov. 2, 2024 Office Action issued in Chinese Patent Application No. 202280068701.1.

Oct. 29, 2024 Office Action issed in Japanese Patent Application No. 2024-522077.

* cited by examiner

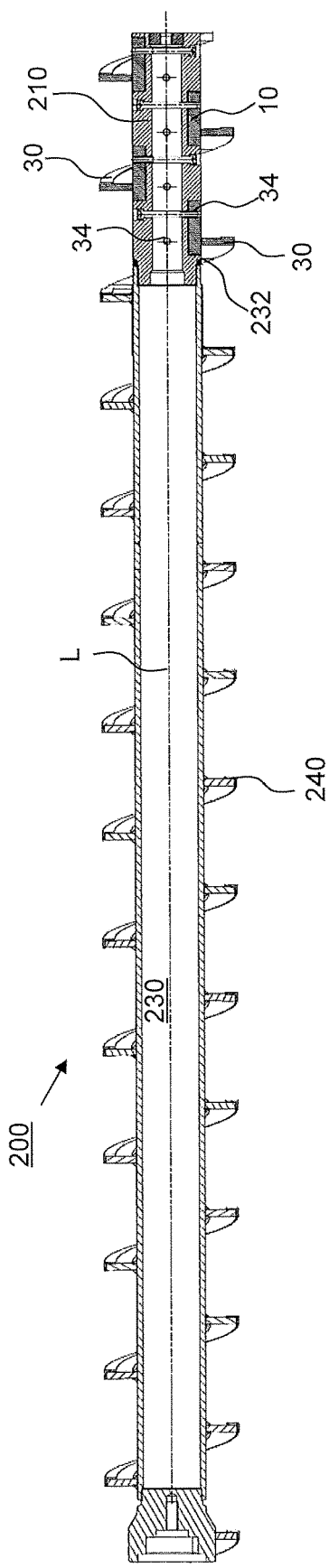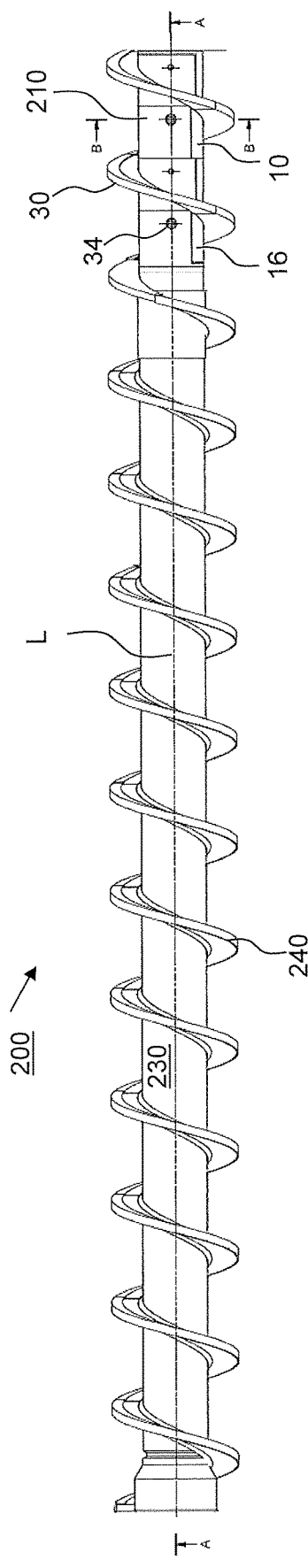
Fig. 2
Fig. 3

HELICAL SCREW CONVEYOR UNIT, WORM SHAFT, WORM EXTRUDER, AND METHOD FOR PROVIDING A WORM SHAFT

TECHNICAL FIELD

The present invention relates to a helical screw conveyor unit.

The present invention furthermore relates to a worm shaft, in other words a conveyor worm.

The present invention furthermore relates to a worm extruder.

The present invention finally relates to a method for providing a worm shaft.

PRIOR ART

The general construction of a worm shaft for use in a worm extruder, and of a worm extruder for dewatering a suspension, is described for example in the documents EP 1 072 574 A2, US 2017/08778 A1 and EP 2 792 739 A1.

The document EP 1 072 574 A2 discloses a fermentation plant with a fermenter and with a dewatering device in the form of a cylindrical worm conveyor. Said worm conveyor extends along a linear axis. As shown in FIGS. 1 to 3, the helix elements form a fixed unit with the worm shaft.

The document US 2017/08778 A1 discloses a worm extruder for dewatering an aqueous suspension of organic material. The device has an extruder chamber in which an extruder worm with helix elements winds in helicoidal form and is mounted so as to be rotatable about its longitudinal axis. In order to allow easy and fast servicing of the worm extruder, US 2017/08778 A1 discloses the provision of multi-part screen baskets which can be pivoted up and which allow easy accessibility to the extruder chamber and allow a screen exchange to be performed by a single person.

The document EP 2 792 739 A1 discloses a double worm shaft in an extruder chamber, as is known for example for cell breakdown extruders. The helical screw conveyor units have so-called clearing tines on the mutually adjacently situated worm shafts.

Anaerobic digestion (AD) is a biological process that allows energy recovery from residual organic material, in particular green waste, by conversion into biogas. The substrate is digested under anaerobic conditions in a fermenter. Here, fermentation material contained in the waste substances is mixed with liquid, and the fermentation material suspension thus obtained is anaerobically fermented in a fermenter.

The digestate formed during the fermentation of the fermentation material suspension is dewatered by means of a worm extruder, wherein, as press water is separated off, a press cake with an increased dry substance fraction in relation to the digestate is obtained. After the substrate exits the fermenter, it is thus separated into solid and liquid digestion residues by a worm extruder.

A worm extruder substantially has an inner worm shaft, with helicoidally winding helix elements, and a screen drum which encases the worm shaft, or a screen cylinder. The digestate for dewatering is pumped via a digestate inlet into the screen drum. The worm shaft rotates and thus conveys the digestate in the direction of a press cake outlet, where there is situated a resistance, for example a counterpressure cone, against which the digestate is pressed. The press water is drained via a press water outlet.

The further the digestate is transported forward, that is to say in the direction of the resistance, the greater is the volume reduction, and the higher is the pressure on the digestate. Even more liquid is thus pressed out of the digestate, which liquid is drained as press water. The dewatered press cake exits the worm extruder via a press cake outlet.

During the operation of the worm extruder, the helix elements become worn over time. This wear occurs more quickly the more pressure is exerted on the digestate by the helix elements, and is particularly pronounced in the front region, situated close to the press cake outlet, of the worm shaft. Wear causes the pressing point to be shifted rearward, whereby the intensity of the dewatering of the digestate is reduced. Worn helix elements must be serviced or exchanged.

As shown in FIGS. 2 and 3 of US 2017/08778 A1, the helix elements are normally fixedly connected to the shank of the worm shaft, for example by welding. In the event of wear of individual helix elements, it is thus necessary for extensive welding work to be performed, or the entire worm shaft must be replaced.

The document EP 0098 340 A1 has disclosed a worm pump for conveying solid and granular material. In order to arrange the end regions, which are subject to particularly intense wear, of the worm helix so as to be exchangeable, exchangeable sleeves are provided in the end region, which sleeves can be removed axially from the worm shaft. To exchange the sleeves, the worm shaft must be dismounted from the worm pump.

Furthermore, the document GB 859 416 A discloses a worm helix conveyor with exchangeable helix elements which can be fitted in the form of a sleeve. In order to make it possible for individual portions of the worm shaft to be dismounted for servicing and repair work, the worm shaft is constructed from multiple sleeve-like longitudinal portions that fit together. Said longitudinal portions are detachably fastened by means of semicircular shell-like bearings to the shank of the worm shaft. After the bearings have been released, the sleeve-like longitudinal portions can be removed from the shank of the worm shaft in an axial direction, for which purpose the worm shaft must be dismounted from its bearing at least at one side.

In order to eliminate the need for cumbersome welding work to remove and repair the vanes of a worm conveyor after they have become worn, the document CN 212 831 025 U discloses fastening the vanes to the shaft by means of a groove and screws. The vanes are in each case separate paddle-like elements that are screwed independently of one another to the shaft.

Presentation of the Present Invention: Problem, Solution, Advantages

The invention is based on the object of further developing a helical screw conveyor unit of the type mentioned in the introduction, and a worm shaft of the type mentioned in the introduction, and a worm extruder of the type mentioned in the introduction, and a method of the type mentioned in the introduction, such that the helical screw conveyor unit can be serviced with little outlay on servicing. In particular, it is the intention that the helical screw conveyor unit, which is configured as an exchangeable element for a helix, be exchangeable without the need for the worm shaft to be dismounted from its bearings for this purpose. It is furthermore sought to lower the servicing costs for the worm shaft.

Said object is achieved by exemplary embodiments disclosed in this application. Advantageous embodiments and expedient refinements of the present invention are characterized in the present application.

The invention is consequently based on the fact that the helical screw conveyor unit is installable radially in exchangeable fashion on a fastening region of the shank of the worm shaft. The helical screw conveyor unit can thus be installed as an exchangeable replacement part on a rotatably mounted worm shaft of a worm extruder. The present invention thus allows the helical screw conveyor unit to be quickly exchanged, because, owing to the radial opening of the main body, designed for receiving the shank, of the helical screw conveyor unit, said helical screw conveyor unit can be installed exchangeably on the shank, and can be exchanged even when the shank is mounted, at its axial ends, in at least one rotary bearing.

In the present case, "radially" refers to a direction that is perpendicular to the longitudinal axis (L) of the worm shaft shank or of the main body of the worm shaft. The radial exchangeability thus allows an efficient exchange of the helix elements without the helix shaft being dismounted from its bearings, and with long operating periods of the worm shaft.

The shank of the worm shaft is a rod-like element for transmitting rotational movements. The helical screw conveyor unit may be installed as a detachable replacement part on the fastening region of the shank. The helical screw conveyor unit is thus advantageously configured to be detachably installed on a fastening region of a worm shaft as presented above. Furthermore, the worm shaft is advantageously suitable for being installed in a worm extruder of the type presented above.

For detachably fastening the main body of the helix element to the fastening region, the helical screw conveyor unit has at least one fastening element. The fastening element of the helical screw conveyor units of the type presented above is thus advantageously detachably connectable to the fastening means, in particular to the fastening structure, of the worm shaft of the type presented above.

In one advantageous exemplary embodiment, the main body is a foot element of the helix element, which foot element is arranged at the radially inner region of the helix element. Here, the fastening element is configured to detachably fasten the foot element to the fastening region. Here, the foot element can be mounted in the manner of a foot onto the fastening region, and the helix element extends outward away from the foot element.

In order to easily radially detachably fasten the helix element to the worm shaft, the fastening element may, in its use position, extend radially into a support region, configured for supporting the helical screw conveyor unit, of the shank, and fasten the foot element, which is seated on the fastening region, to the support region.

In one advantageous exemplary embodiment, the support region of the shank has at least two helix elements, each helix element being assigned at least one fastening element, and the fastening elements of the mutually adjacent helix elements being arranged so as to be both axially and radially offset with respect to one another. The fastening element is preferably a socket head screw, and the fastening means is preferably a thread. Alternatively, the fastening element may also interact with a fastening means in the manner of a detachable snap-action fastener.

The inner surface of the main body of the helical screw conveyor unit of the type presented above is preferably configured to be seated, in particular be mounted, on the fastening region of the worm shaft of the type discussed above. In other words, the fastening region is assigned to a region of the worm shaft that is configured for supporting the main body of the helical screw conveyor unit.

In order to make an exchange of the helical screw conveyor unit on the worm shaft particularly straightforward, the inner surface the main body is advantageously shaped such that, as a result of the inner surface of the main body being seated on the fastening region of the worm shaft, the orientation of the helix element of the helical screw conveyor unit on the worm shaft is defined, and radial mobility of the main body on the worm shaft is at least restricted. The inner surface of the main body and the fastening region thus advantageously have a shape or structure that interacts and prevents radial slippage or a rotational movement of the helical screw conveyor unit around the shank. Here, a radial rotational movement of the helical screw conveyor unit around the shank is caused already by the interaction of the shape or structure of the fastening region with the shape or structure of the inner surface of the main body. The fastening means then serves for further or additional fixing. As described in more detail below, this fastening, achieved by way of shape or structure, may be realized for example by means of a square shape of the fastening region. The fastening region is configured for detachably fastening the fastening element of the helical screw conveyor unit and is assigned to a support region, configured for supporting the helical screw conveyor unit, of the shank of the worm shaft. The fastening region has at least one fastening means, for example a fastening structure. The support region advantageously has at least two fastening regions, such that it is advantageously possible for at least two helical screw conveyor units of the type presented above to be detachably fastened to the support region of the worm shaft.

The worm shaft thus advantageously has at least two helical screw conveyor units. Here, the fastening regions of the support region are preferably configured such that adjacent helical screw conveyor units are arranged in each case so as to be axially and radially offset, for example mirror-symmetrically offset, with respect to one another. In this advantageous exemplary embodiment, the worm shaft has at least two helix elements which are arranged so as to be axially and radially offset with respect to one another. Accordingly, the support region has at least two fastening regions which are arranged so as to be axially and radially offset with respect to one another. In this exemplary embodiment, it is advantageously also the case that the fastening elements of the adjacent helical screw conveyor units are arranged so as to be axially and radially offset with respect to one another, for example arranged so as to be offset by 90 degrees, for example perpendicularly with respect to one another.

The helix elements have a partial helix turn, for example one quarter to one half of one helix turn. Multiple adjacent coil elements together form a spiral-shaped or helical or helicoidal helix turn. Multiple helix turns together form the helicoidally or helically or spirally winding helix of the worm shaft. Since it is the case in the present invention that the helix elements are exchangeable, it is possible, in relation to a worm shaft known from the prior art with non-detachable helix elements, to accept increased material wear of said helix elements, and for the resistance of the worm extruder to be increased, for example for the counterpressure cone to be enlarged or lengthened, in order to provide a greater expenditure of force for dewatering the digestate.

The main body of the helical screw conveyor unit has a radial opening. The fastening region can be led through said opening in a radial direction, that is to say in a direction perpendicular to the longitudinal axis (L) of the main body, and arranged on the inner surface of the main body. In other words, the support region can be led through the opening and received in a cavity surrounded by the concave main body.

The fastening element is preferably configured to provide a form-fitting connection between the main body and the support region or shaft body element of the shank, for example a screw such as a socket head screw. Alternatively, it would also be possible for the fastening element to be configured to provide a snap-action connection or a clamping connection.

In order to be able to arrange the main body such that it is supported on the support region, the inner surface of the main body is of complementary design with respect to the fastening region, and the outer side of the main body is concavely curved and runs, preferably in the shape of a half-shell or in the shape of a semicircle, around the longitudinal axis.

The fastening region has at least one seating surface configured for supporting the main body, in particular the inner surface of the main body. In order to prevent slippage of the main body on the seating surface, the inner surface of the lateral surface of the main body advantageously has at least one contour, configured for the positionally fixed arrangement of the main body on the fastening region, and is advantageously of complementary design with respect to the fastening region or with respect to the seating surface of the fastening region. The contour of the inner surface of the main body of the helical screw conveyor unit is preferably U-shaped or n-shaped in cross section.

The helical screw conveyor on the worm shaft can be exchanged particularly quickly and easily if the helix element is shaped such that, as a result of the inner surface of the main body being seated on the fastening region of the worm shaft, the helix element is oriented so as to at least substantially continue the course of the helicoidally or spirally winding helix of the worm shaft.

In order to prevent radial slippage of the main body on the shank, the inner surface of the lateral surface may for example be of right-angled shape, or may be of curved, arcuate or stepped shape. For example, the fastening region may be u-shaped in cross section, and the inner surface of the main body may be n-shaped in cross section, or vice versa.

The support region of the shank may, at least in the region of the fastening region, be configured as a square. Alternatively, the fastening region may be formed by at least one recess or at least one groove of the otherwise cylindrical support region. For example, the fastening region may be a u-shaped or n-shaped recess of the otherwise cylindrical support region. In order to prevent slippage of the helical screw conveyor units on the fastening region, said fastening region advantageously has a square seat.

The helix element has a part or a portion of a helix turn, preferably one half of one helix turn. Alternatively, said helix element may for example also have one third of one helix turn or one quarter of one helix turn. The helical screw conveyor unit has at least one helix unit, preferably multiple, for example four, helix units arranged adjacent to one another. For a connection with an accurate fit, helix elements of mutually adjacently arranged helical screw conveyor units may be welded to one another and jointly ground.

It is advantageous if the fastening element, in its use position, extends radially through the support region and projects into the main body or through the main body of at least one helical screw conveyor unit arranged on the support region. The fastening element particularly preferably projects, at its end that emerges from the support region, into the main body of a helical screw conveyor unit. Thus, for the exchange of the helical screw conveyor unit, the fastening element only needs to be partially released, for example only needs to be released from the main body of the helical screw conveyor unit, but can still remain fastened to the support region. This prevents loss of the fastening element.

The screw shaft advantageously has at least one helical screw conveyor element of the type presented above, the helical screw conveyor element being detachably fastenable to the fastening region.

In addition to the helical screw conveyor element, the shank may furthermore have a cylindrical shaft body which extends along the longitudinal axis and which has at least one shaft body helix winding helicoidally around the shaft body. The fastening region of the support region, which likewise extends along the longitudinal axis, has a cross-sectional diameter smaller than that of the cylindrical shaft body. This makes it possible for the helical screw conveyor unit to be arranged on the support region such that the top side of the lateral surface of said helical screw conveyor unit terminates flush with the cylindrical main body.

The support region is advantageously arranged eccentrically, in particular on a near-terminal region, for example on a terminal region, of the cylindrical shaft body. The worm shaft can thus be arranged in a worm extruder such that the at least one exchangeable helix element is arranged in the front region, situated close to the press cake outlet, of the worm extruder. The exchange of only the front helices, which are most affected by wear, makes it possible for the worm shaft to be serviced easily, quickly and at low cost.

In one advantageous embodiment of the method of the present invention, the worm shaft is serviced by virtue of
at least one fastening means, which fastens a first helical screw conveyor unit to the fastening region, being released,
the first helical screw conveyor unit being removed from the worm shaft,
a further helical screw conveyor unit being arranged on the fastening region and
being fastened detachably to the fastening region by a fastening means assigned to said further helical screw conveyor unit.

The present invention finally relates to the use of at least one worm shaft of the type presented above in a worm extruder of the type presented above for the purposes of separating solid and liquid digestion residues from residual biogenic substances, in particular green waste, treated by means of a fermenter.

BRIEF DESCRIPTION OF THE DRAWINGS

As already discussed above, there are various possibilities for the advantageous embodiment and refinement of the teaching of the present invention. Embodiments, features and advantages of the present invention will be discussed in more detail below, inter alia on the basis of the exemplary embodiment illustrated by FIGS. 1 to 7.

In the figures:

FIG. 2 shows the worm shaft from FIG. 1 in a longitudinal sectional illustration;

FIG. 3 shows a side view of the worm shaft from FIG. 1;

Identical or similar embodiments, elements or features are denoted by identical reference designations in FIGS. 1 to 7.

Best Way of Implementing the Invention

Figure 1:
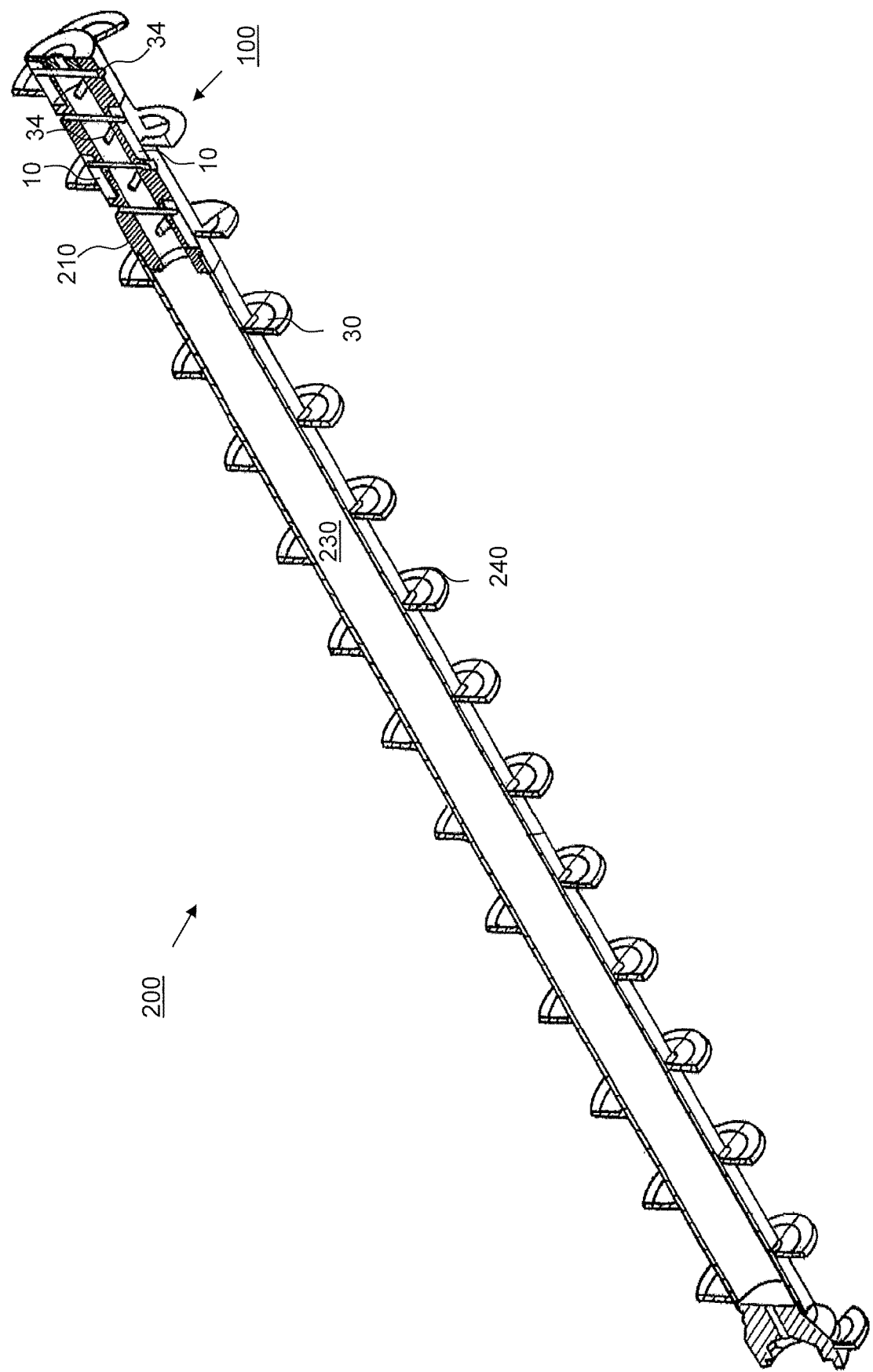
FIG. 1 shows, in a perspective illustration, a longitudinal section through a first exemplary embodiment of a worm shaft according to the present invention, having a helical screw conveyor unit according to the present invention arranged detachably thereon, which helical screw conveyor unit is exchangeable in accordance with the method of the present invention.
Figure 4:
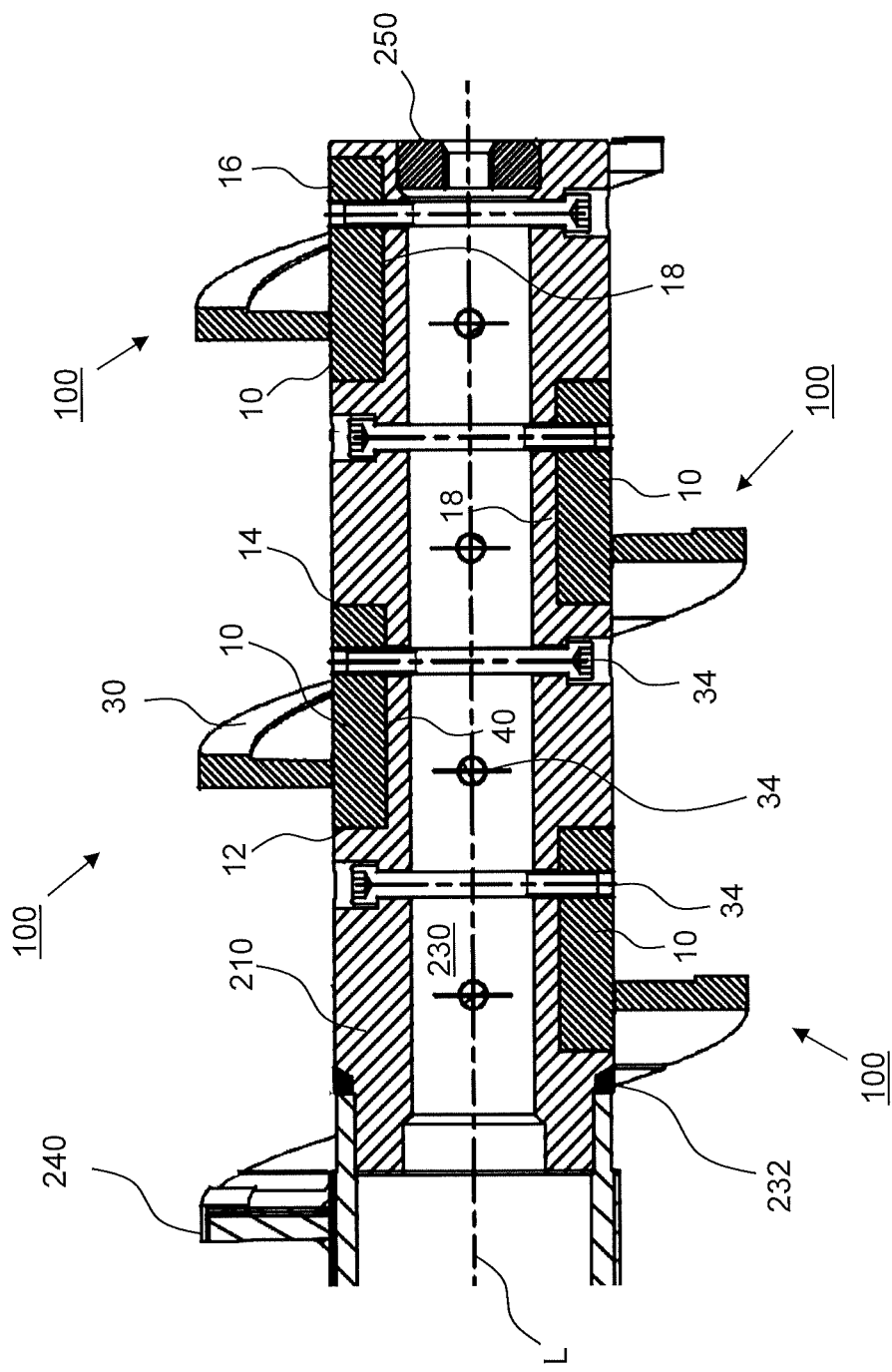
FIG. 4 shows a detail view of the front region of the worm shaft from FIG. 2.
Figure 5:
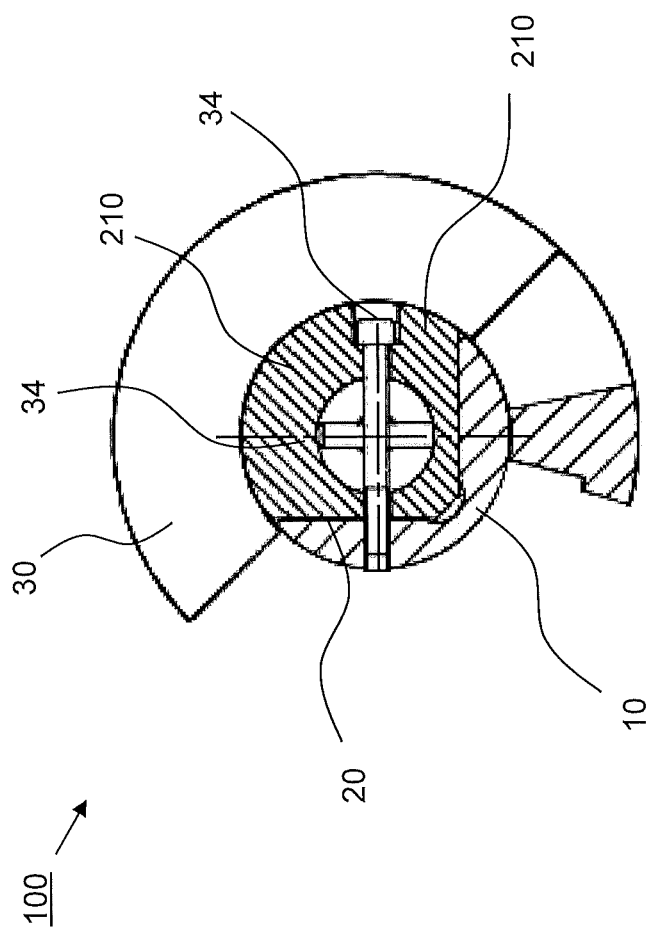
FIG. 5 shows a cross section through the helical screw conveyor unit from FIG. 1 along the line B-B shown in FIG. 3.

FIG. 1 shows an exemplary embodiment of a helical screw conveyor unit 100 for a worm shaft 200. The helical screw conveyor unit 100 has a main body 10 that extends along a longitudinal axis L. The main body has two end regions which extend perpendicularly with respect to the longitudinal axis, in other words are situated opposite one another in the direction of the longitudinal axis. The end regions 12, 14 are connected to one another by a lateral surface, with at least one helicoidally winding helix element 30 being arranged around a top side 16 or outer surface of the lateral surface.

In the exemplary embodiment shown in FIGS. 1 to 3, the worm shaft 200 has multiple, for example two, helix elements 30. For a connection of the helix elements 30 with an accurate fit, these may be welded to one another and jointly ground.

The at least one helix element 30 has a partial helix turn, in particular one quarter to one half of one helix turn. The main body is concavely curved, that is to say inwardly arched, and has a radial opening 20. In other words, the main body is hollow and runs in curved fashion around the longitudinal axis L. The main body preferably runs in the shape of a circular segment, for example in the manner of a half-shell, around the longitudinal axis L.

The helical screw conveyor unit 100 is configured for exchangeable installation in a worm shaft 200, preferably in a worm shaft 200 of a worm extruder 300 that is configured for dewatering digestate obtained by anaerobic digestion of organic material.

Figure 6:
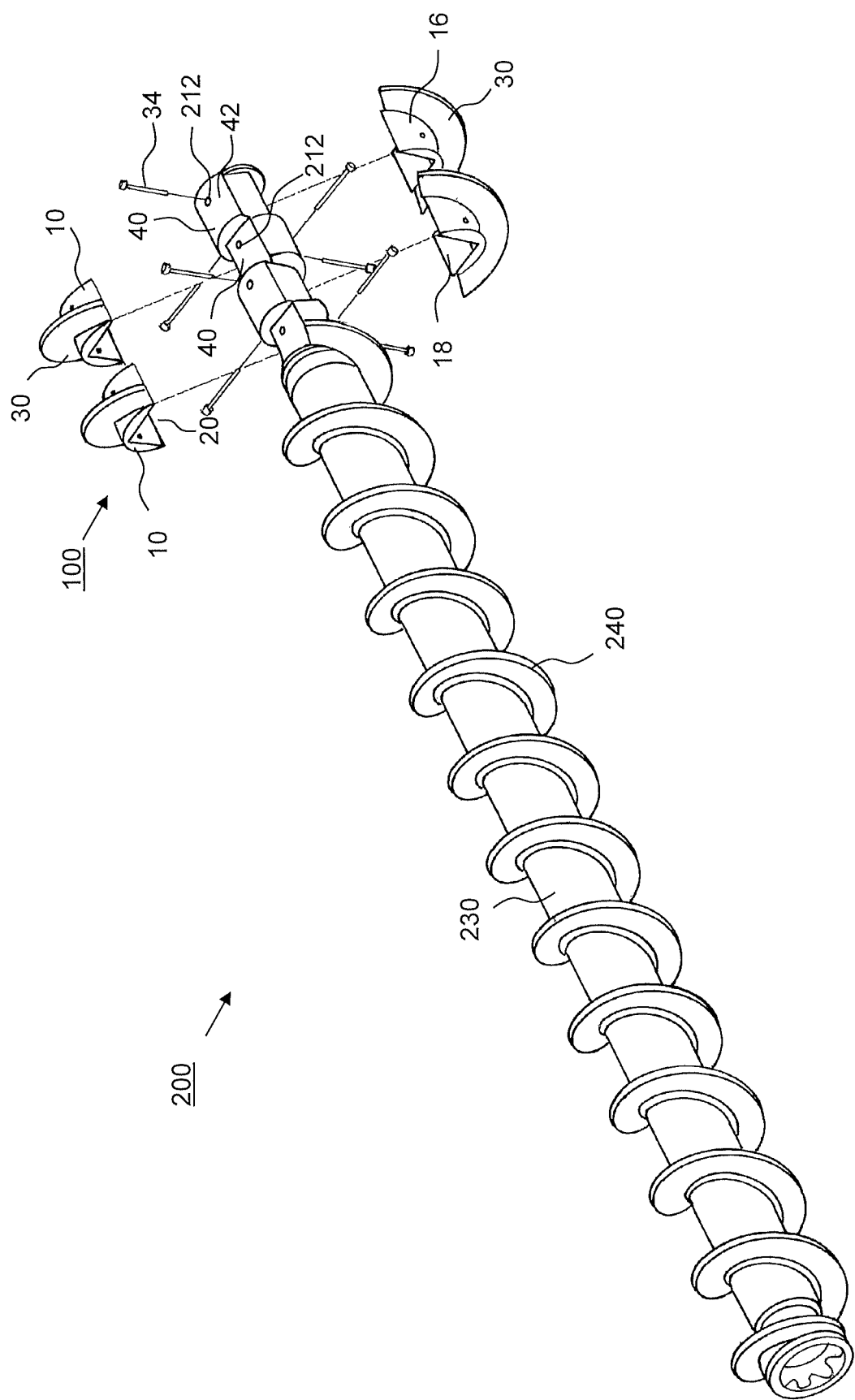
FIG. 6 shows the worm shaft from FIG. 1 in an exploded illustration.

FIG. 6 shows an exploded illustration of the worm shaft 200. Said worm shaft has four helical screw conveyor units 100 which together form two encircling helices. Respectively adjacent helical screw conveyor units 100 are arranged so as to be radially offset with respect to one another by 180 degrees, that is to say mirror-symmetrically. For the detachable fastening of the main body 100 to the fastening regions 40 of the support region 210, the helical screw conveyor units each have two socket head screws 34. The fastening regions 40 are shaped in the manner of a partial square, or are of rectangular shape. Those regions of the support region 210 which are situated opposite the helical screw conveyor units 100 or opposite the fastening regions 40 are configured as filler bodies. These protect and stabilize the support region 210. Said filler bodies may be fixedly connected to the support region 210, for example formed integrally with the support region 210, or detachably fastened to the support region 210. The filler bodies are concavely curved about the longitudinal axis L.

Figure 7:
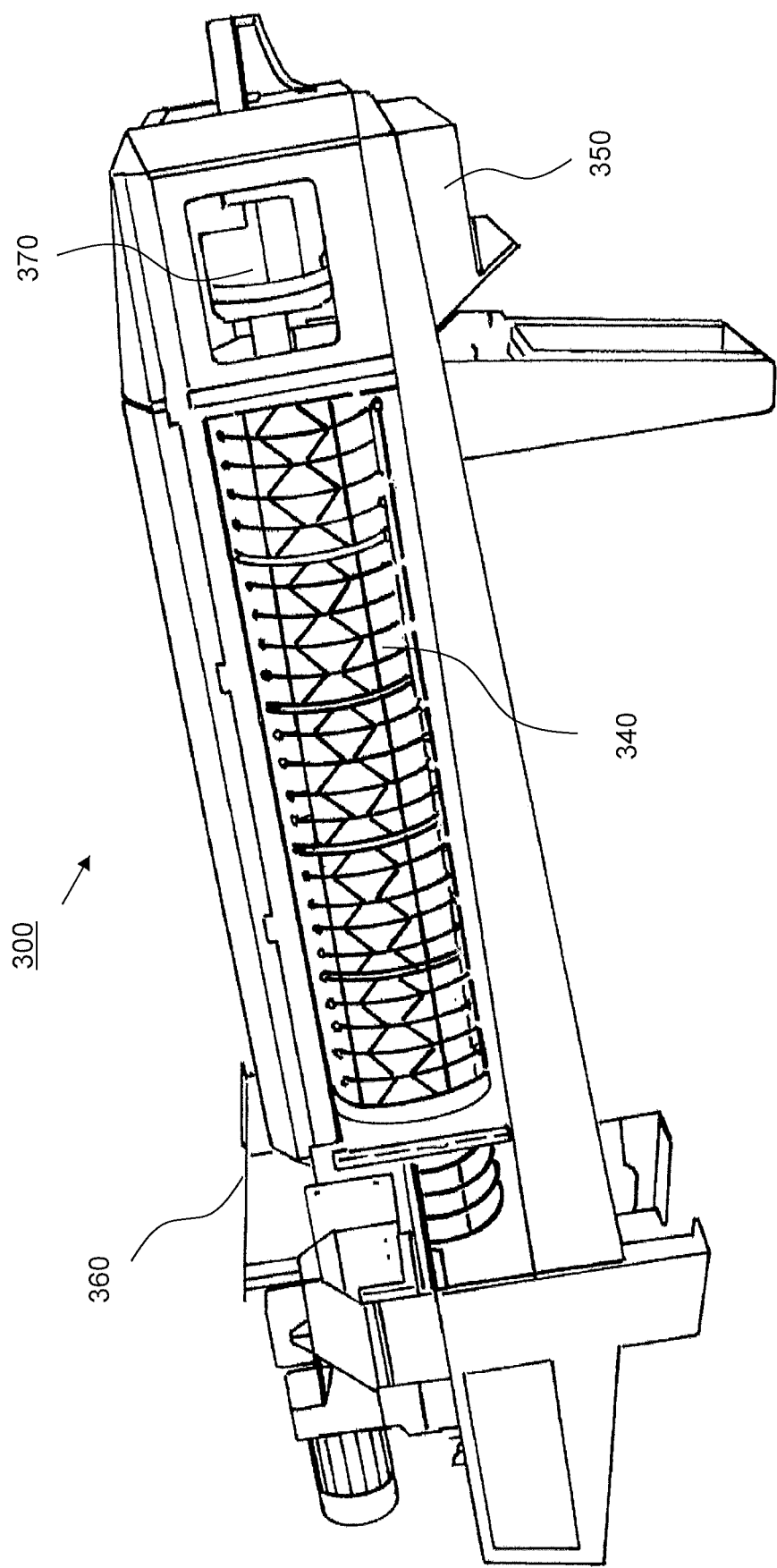
FIG. 7 shows an exemplary embodiment of a worm extruder according to the present invention with the worm shaft from FIG. 1.

As shown in FIG. 7, the worm extruder 300 has an inner worm shaft 200, with helicoidally winding helix elements 30, 210 which extend away outward, and has a screen drum 340 which encases the worm shaft 200. The screen drum 340 may have pivotable screen shells, allowing easy access to the worm shaft and a fast exchange of screen parts and wearing parts.

For exchangeable installation in a worm shaft 200, the helical screw conveyor unit 100 has an inner surface 18, configured for receiving a support region 210 of a shank 230, on the lateral surface of the main body 10, and at least one fastening element 34 configured for detachably fastening the inner surface 18 to the support region 210.

The helical screw conveyor unit 100 is thus a detachably fastenable or exchangeable element for a worm shaft 200.

In an exemplary embodiment of the present invention that is not shown here, the worm shaft 200 may have exclusively exchangeable helix elements 30. It is alternatively possible, as shown in FIGS. 1 to 7, for only a partial region, for example a front region that is situated close to a press cake outlet 310 in a use position, of the worm shaft 200 to be configured as an exchangeable helical screw conveyor unit 100.

The worm shaft shown in FIGS. 1 to 7 has not only the exchangeable helical screw conveyor unit 100 but also a shank 230 with a cylindrical shaft body and with a shaft body helix 240 winding helicoidally around the shank 230. In the region of the cylindrical shaft body, the shaft body helix 240 is non-detachably connected to the shank 230, for example formed integrally with the shank 230 or welded to the shank 230.

The support region 210 of the helical screw conveyor unit 100 may be non-detachably connected, for example using the technique of welding, for example by means of a root seam 232, to the cylindrical shaft body. Alternatively, the support region 210 may also be formed integrally with the cylindrical shaft body of the shank 230.

The helical screw conveyor units 100 are arranged such that the helix elements 30 continue the course of the shaft body helix 240 of the cylindrical shaft body, and with this form a common shaft body helix unit.

The main body 10 of the helical screw conveyor unit 100 is concavely curved. Here, the main body may be configured such that, in the use position of the worm shaft 200, the support region 210 is fully encased (not shown) by the main bodies of the helical screw conveyor units 100 arranged on the support region 210. For example, in each case two helical screw conveyor units 100 configured as half-shells may fully encase the shaft body element 210.

Alternatively, the main body 10 may be a foot element 32 of the helix element 30, which foot element is arranged at the radially inner region of the helix element 30 and can be exchangeably arranged in a fastening region 40, configured as a groove, of the support region 210.

In the exemplary embodiment shown in FIGS. 1 to 7, the helix frequency of the helix elements 30 is identical to the helix frequency of the shaft body helix 240. It would however also be possible for the helix frequency or the pitch of the helix elements 30 to increase in relation to the helix frequency of the shaft body helix 240.

For the rotatable mounting of the worm shaft 200 in the worm extruder 300, said worm shaft has at least one rotary bearing 250. In order to relieve the transmission of the worm extruder 300 of radial and axial forces, the worm shaft 200 may have a double bearing configuration. This allows longer service lives of the worm extruder 300.

A preferred material for the helical screw conveyor unit 100 of the type presented above, and for the worm shaft 200 of the type presented above, is steel.

LIST OF REFERENCE NUMERALS

10 Main body, in particular foot element of the helix element 30
12 First end region of the main body, in particular first end region, extending perpendicular to the longitudinal axis, of the main body
14 Second end region of the main body, in particular second end region, extending perpendicular to the longitudinal axis, of the main body
16 Top side, in particular outer side, of the lateral surface of the main body 10
18 Inner side of the lateral surface of the main body
20 Radial or concave opening of the main body 10
30 Helix element of the helical screw conveyor unit 100
34 Fastening element of the helix element 30
40 Fastening region, in particular U-shaped fastening region, square or receiving groove, of the main body 10
42 Filler body
100 Helical screw conveyor unit
200 Worm shaft or conveyor worm or extruder worm, in particular rod-like worm shaft shank with helicoidally or spirally winding helix elements 240, 30
210 Shaft body element, or support region, configured for supporting the main body 10 of the helical screw conveyor unit 100, of the worm shaft shank 230, in particular shank seating region or support region of the shank 230 of the worm shaft 200
212 Fastening means, in particular thread, of the shaft body element 210
230 Shank or rod-like main body of the worm shaft 200, in particular with cylindrical shaft body and with support region 210 configured for supporting the main body 10 of the helical screw conveyor unit 100
232 Weld seam, in particular root seam, for connecting the cylindrical shaft body 230 to the main body 10
240 Spirally or helically or helicoidally winding shaft body helix, or helix element, of the worm shaft 200
250 Rotary bearing (cf. FIG. 4)
300 Worm extruder
340 Screen drum
350 Press cake outlet
360 Digestate inlet
370 Resistance, in particular counterpressure cone
L Longitudinal axis

The invention claimed is:

1. A worm shaft for use in a worm extruder, comprising a shank which extends along a longitudinal axis and which has a helicoidally or spirally winding helix,
   a helical screw conveyor unit configured as an exchangeable element for the helicoidally or spirally winding helix,
   the helical screw conveyor unit comprising a main body extending along the longitudinal axis, the main body having two axial end regions and a lateral surface that connects the end regions to one another, at least one helicoidally winding helix element being arranged on a top side of the lateral surface and extending radially outward away from the top side wherein
   the top side of the lateral surface is concavely curved in shell-like form about the longitudinal axis, and the main body has a radial opening, the radial opening being configured such that a fastening region of the shank can be led through the opening in a direction perpendicular to the longitudinal axis and can be arranged in a cavity formed by the main body,
   the helix element has at most one half of one helix turn,
   the lateral surface of the main body has an inner surface configured for being seated on the fastening region, and
   the helical screw conveyor unit has at least one first fastener configured for detachably fastening the main body to the fastening region,
   the worm shaft further comprising at least one second fastener configured for detachably fastening the first fastener, and
   wherein the shank has a cylindrical shaft body and the fastening region, the fastening region being assigned to a support region, configured for supporting the main body of the helical screw conveyor unit of the shank, and having a cross-sectional diameter smaller than that of the cylindrical shaft body.

2. The worm shaft as claimed in claim 1, wherein the support region is arranged eccentrically.

3. The worm shaft as claimed in claim 1, wherein the support region has at least two helical screw conveyor units each having a configuration of the helical screw conveyor unit, the helical screw conveyor units being arranged such that the helical elements of the helical screw conveyor units continue the course of the helicoidally or spirally winding helix of the cylindrical shaft body and, with this, form a common shaft body helix unit.

4. The worm shaft as claimed in claim 1, wherein the worm shaft has at least two helical screw conveyor units each having a configuration of the helical screw conveyor unit which are in each case arranged adjacent to one another and together form one full helix turn that fully encircles the shank once.

5. The worm shaft as claimed in claim 2, wherein the support region has at least two helical screw conveyor units each having a configuration of the helical screw conveyor unit, the helical screw conveyor units being arranged such that the helical elements of the helical screw conveyor units continue the course of the helicoidally or spirally winding helix of the cylindrical shaft body and, with this, form a common shaft body helix unit.

6. The worm shaft as claimed in claim 1, wherein the worm shaft has at least two helical screw conveyor units each having a configuration of the helical screw conveyor unit which are in each case arranged adjacent to one another and together form one full helix turn that fully encircles the shank once.

7. The worm shaft as claimed in claim 1, wherein the second fastener is configured to interact with the first fastener of the helical screw conveyor unit such that the helical screw conveyor unit is detachably fastenable to the fastening region of the worm shaft.

8. The worm shaft as claimed in claim 1, wherein the fastening region of the worm shaft is shaped such that a radial movement of the main body seated on the fastening region is at least restricted.

9. The worm shaft as claimed in claim 1, wherein at least two of the fastening regions which are formed by at least one recess or at least one groove of the otherwise cylindrical shaft body and which are arranged so as to be radially and axially offset with respect to one another.

10. The worm shaft as claimed in claim 1, wherein the main body runs in a shape of a semicircle or in a shape of a half-shell about the longitudinal axis, and the helix element has one half of one helix turn.

11. The worm shaft as claimed in claim 1, wherein the inner surface of the main body is shaped such that, as a result of the inner surface of the main body being seated on the fastening region of the worm shaft, an orientation of the helix element of the helical screw conveyor unit on the worm shaft is defined, and radial mobility of the main body on the worm shaft is at least restricted.

12. The worm shaft as claimed in claim 11, wherein, for an orientation of the helix element on the worm shaft, the inner surface of the lateral surface has a contour of a complementary shape with respect to the fastening region of the shank.

13. The worm shaft as claimed in claim 10, wherein the helix element is shaped such that, as a result of the inner surface of the main body being seated on the fastening region of the worm shaft, the helix element is at least substantially oriented so as to continue the course of the helicoidally or spirally winding helix of the worm shaft.

14. A worm extruder for dewatering a suspension comprising an extruder chamber in which a worm shaft having a helicoidally winding helix element is mounted so as to be rotatable about its longitudinal axis, wherein the worm shaft is comprises:
- a shank which extends along a longitudinal axis and which has a helicoidally or spirally winding helix,
- a helical screw conveyor unit configured as an exchangeable element for the helicoidally or spirally winding helix,
- the helical screw conveyor unit comprising a main body extending along the longitudinal axis, the main body having two axial end regions and a lateral surface that connects the end regions to one another, at least one helicoidally winding helix element being arranged on a top side of the lateral surface and extending radially outward away from the top side, wherein
- the top side of the lateral surface is concavely curved in shell-like form about the longitudinal axis, and the main body has a radial opening, the radial opening being configured such that a fastening region of the shank can be led through the opening in a direction perpendicular to the longitudinal axis and can be arranged in a cavity formed by the main body,
- the helix element has at most one half of one helix turn,
- the lateral surface of the main body has an inner surface configured for being seated on the fastening region, and
- the helical screw conveyor unit has at least one first fastener configured for detachably fastening the main body to the fastening region,
- the worm shaft further comprising at least one second fastener configured for detachably fastening the first fastener, and
- wherein the shank has a cylindrical shaft body and the fastening region, the fastening region being assigned to a support region, configured for supporting the main body of the helical screw conveyor unit of the shank, and having a cross-sectional diameter smaller than that of the cylindrical shaft body, and
- wherein the shank of the worm shaft having at least two helical screw conveyor units, and the helical screw conveyor units each having a configuration of the helical screw conveyor unit.

* * * * *